United States Patent
Pohan et al.

(10) Patent No.: US 7,476,025 B2
(45) Date of Patent: Jan. 13, 2009

(54) SHADOW MASK FOR AN X-RAY DETECTOR, COMPUTED TOMOGRAPHY UNIT HAVING A SHADOW MASK, AND A METHOD FOR ADJUSTING A SHADOW MASK

(75) Inventors: Claus Pohan, Baiersdorf (DE); Mario Reinwand, Breitbrunn (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 99 days.

(21) Appl. No.: 11/365,583

(22) Filed: Mar. 2, 2006

(65) Prior Publication Data

US 2006/0198493 A1 Sep. 7, 2006

(30) Foreign Application Priority Data

Mar. 3, 2005 (DE) .................. 10 2005 009 817

(51) Int. Cl.
*A61B 6/08* (2006.01)
(52) U.S. Cl. ..................................... 378/205
(58) Field of Classification Search .................. 378/19, 378/146, 154, 155, 205
See application file for complete search history.

(56) References Cited

U.S. PATENT DOCUMENTS

| | | | | |
|---|---|---|---|---|
| 4,298,800 A | * | 11/1981 | Goldman | ..................... 378/19 |
| 5,131,021 A | * | 7/1992 | Gard et al. | ..................... 378/19 |
| 5,400,379 A | | 3/1995 | Pfoh et al. | |
| 6,947,516 B2 | * | 9/2005 | Okumura et al. | ............. 378/19 |
| 2006/0280293 A1 | * | 12/2006 | Hardesty | ..................... 378/205 |

FOREIGN PATENT DOCUMENTS

JP 2004-283343 10/2004

\* cited by examiner

*Primary Examiner*—Chih-Cheng G Kao
(74) *Attorney, Agent, or Firm*—Harness, Dickey & Pierce PLC

(57) ABSTRACT

A shadow mask and method for adjustment are disclosed. The shadow mask may be for an X-ray detector including detector elements, which may further be provided for a computed tomography unit, for example. The shadow mask has a mask plate with holes of which each is assigned a detector element. At least one adjusting hole of the mask plate includes enlarged dimensions in such a way that it is adapted to the dimensions of at least two detector elements. The adjusting hole serves for the method of adjusting the shadow mask over the X-ray detector. Measurement signals of the detector elements that are assigned to the at least one adjusting hole, are determined by using X-radiation. The shadow mask and the X-ray detector are adjusted relative to one another on the basis of a comparison of the measurement signals of the detector elements.

8 Claims, 4 Drawing Sheets

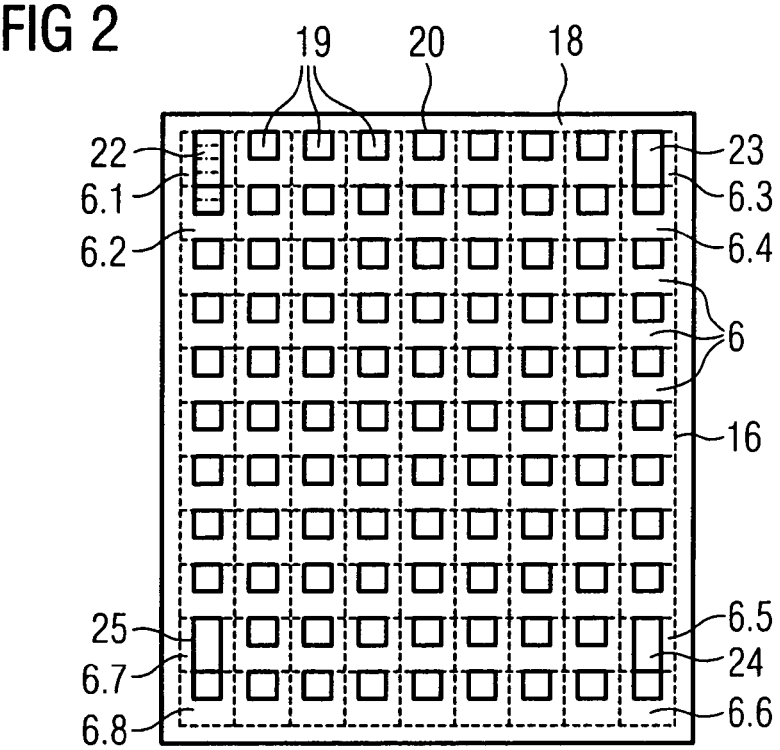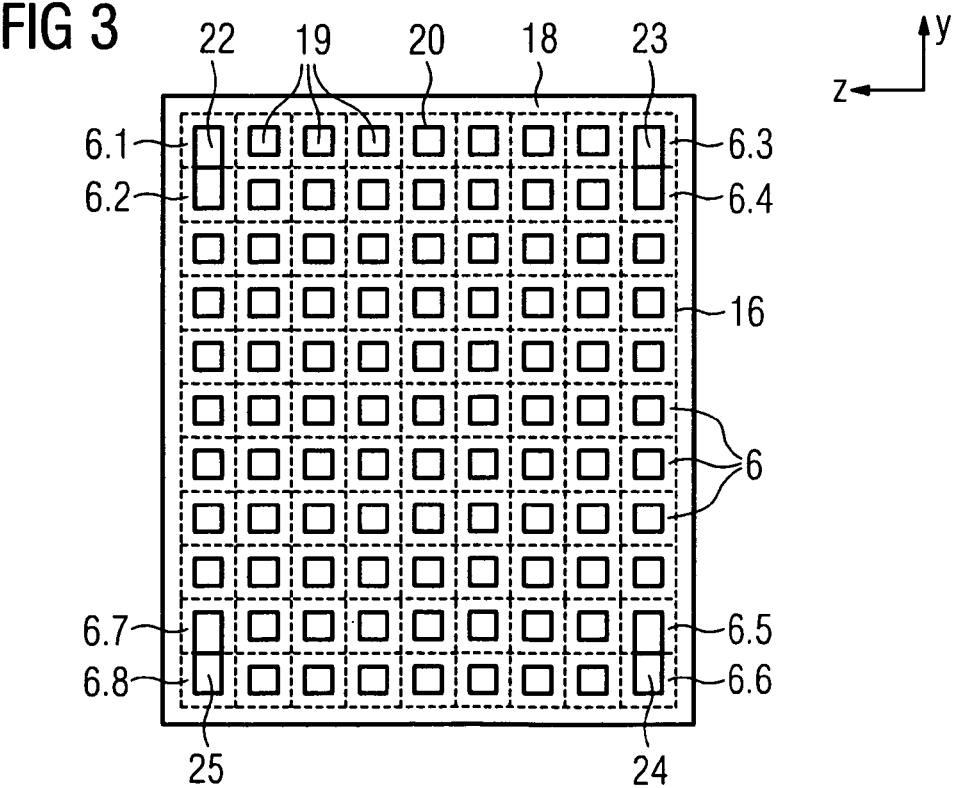

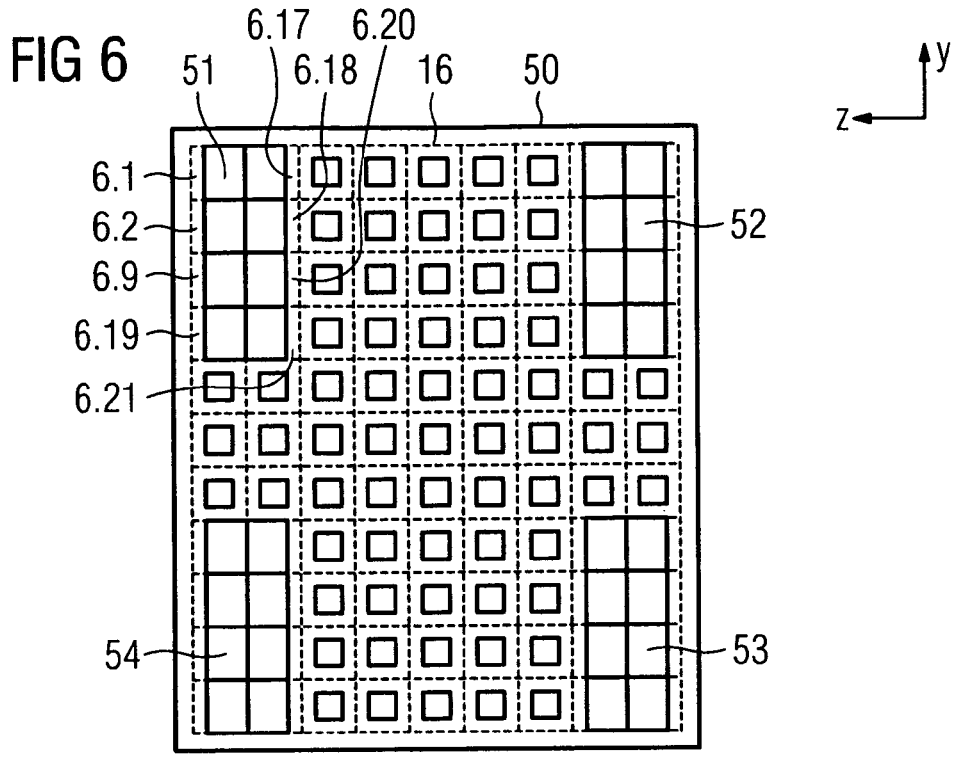
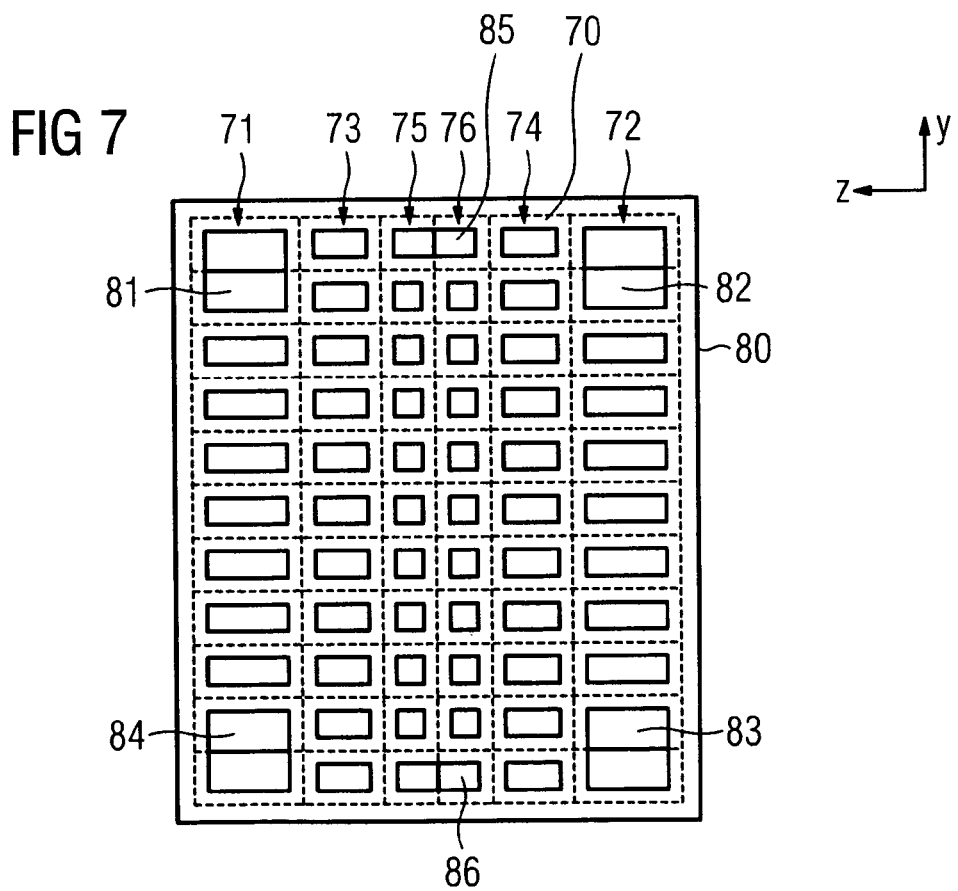

SHADOW MASK FOR AN X-RAY DETECTOR, COMPUTED TOMOGRAPHY UNIT HAVING A SHADOW MASK, AND A METHOD FOR ADJUSTING A SHADOW MASK

The present application hereby claims priority under 35 U.S.C. §119 on German patent application number DE 10 2005 009 817.7 filed Mar. 3, 2005, the entire contents of which is hereby incorporated herein by reference.

FIELD

The invention generally relates to a shadow mask for an X-ray detector comprising detector elements, and/or to a computed tomography unit having such a shadow mask. The invention also generally relates to a method for adjusting a shadow mask over an X-ray detector, having detector elements, of an X-ray device.

BACKGROUND

The aim in imaging methods, in particular in digital recording methods and also used in medical imaging, for example in computed tomography, is to increase the resolution of generated images. This can be achieved, for example, by reducing the pixel surface of a detector in the case of an X-ray device by reducing the detection surface of an X-ray detector. It is known for this purpose to cover the pixel surface at least partially with a perforated metal sheet or, in the case of optical detectors, with a shadow mask.

JP 2004-283343-A discloses for example an X-ray computer tomograph in which a shadow mask is arranged between an X-ray source and an X-ray detector. The shadow mask has a multiplicity of holes such that the projection surface of an X-ray projection is smaller than the detector surface made available by the X-ray detector. As already mentioned, the resolution of an image determined with the aid of the X-ray computed tomograph is increased with the aid of. the shadow mask.

Since the shadow mask is generally not required for all the measurement operations in an imaging unit, this is used according to requirements. However, there proves to be a problem here in adjusting the shadow mask, if required, above the pixel matrix of the detector used.

SUMMARY

It is an object of at least one embodiment of the invention to specify a shadow mask for a computed tomography unit, in particular, with the aid of which the adjusting of the shadow mask and of an X-ray detector relative to one another is simplified. A further object of at least one embodiment of the invention resides in specifying a suitable method for adjusting the shadow mask and an X-ray detector relative to one another.

An object relating to at least one embodiment of the shadow mask may be achieved by way of a shadow mask for an X-ray detector comprising detector elements, having a mask plate made from a material that absorbs X-radiation which is provided with holes, each hole being substantially adapted with regard to its dimensions to the dimensions of the detector element to which the hole is assigned, at least one hole of the mask plate having dimensions enlarged in such a way that it is adapted to the dimensions of at least two detector elements. The shadow mask according to at least one embodiment of the invention therefore has at least one hole with enlarged dimensions such that, when the shadow mask and the X-ray detector are aligned relative to one another by using X-radiation, it is possible to compare with one another the measurement signals of the two detector elements that are assigned to the hole of the mask plate which has an enlarged dimension.

In particular, the ratio or the difference in the measurement signals of the detector element can be used to derive whether or not the shadow mask is aligned precisely above the detector element of the X-ray detector. If, for example, detector elements of the same dimensions, that is to say the same detector surface, are assumed, it follows that when the shadow mask is aligned precisely above the X-ray detector the ratio of the measurement signals of the two detector elements that are assigned to the hole of the enlarged dimensions in the mask plate is at least substantially equal to one, or the difference between the measurement signals is at least substantially equal to zero. If the ratio is not equal to one, or the difference is not equal to zero, the shadow mask and the X-ray detector are preferably adjusted relative to one another until the ratio of 1:1 or the difference of zero is yielded.

Although it is said above that the dimensions of the holes of the shadow mask are adapted to the dimensions of the detector elements, this does not mean that the holes and the detector elements, assigned to them, of the X-ray detector have the same dimensions. Rather, each hole in the shadow mask has smaller dimensions than the detection surface of the detector element to which the respective hole is assigned. With regard to their dimensions, the holes are adapted to the detector elements, assigned to them, of the X-ray detector in such a way that X-radiation is always applied substantially to the same size of surface fraction of a detector element of the X-ray detector, given an X-ray detector with detector elements of the same dimensions and given precise positioning of the shadow mask above the X-ray detector.

The hole of the mask plate with enlarged dimensions is designed in such a way that that surface of each detector element assigned to the hole of enlarged dimensions to which X-radiation can be applied is substantially the same given precise alignment of the shadow mask and the X-ray detector relative to one another. It thus becomes clear that the shadow mask and the X-ray detector can be aligned relative to one another in a simple way by the comparison of the measurement signals of the detector elements that are assigned to the hole with enlarged dimensions.

According to one variation of at least one embodiment of the invention, the shadow mask generally has a number of holes with enlarged dimensions in order, on the basis of the determined measurement signals at various points, to be able to achieve an alignment of the shadow mask and the X-ray detector relative to one another that is as precise as possible. In accordance with one variant of at least one embodiment of the invention, the hole with enlarged dimensions extends over at least two detector elements lying in a specific direction. It is possible in this way to check the alignment of the shadow mask and the X-ray detector relative to one another for this specific direction with the aid of the measurement signals of the detector elements. If a number of holes of enlarged dimensions that lie in various directions are selected, the alignment of the shadow mask and the X-ray detector relative to one another can be checked and performed for the respective direction with the aid of the measurement signals.

A further variant of at least one embodiment of the invention provides that the hole with enlarged dimensions extends over at least three detector elements of which two detector elements lie in different directions. If the hole is, for example, of L-shaped design, an adjustment path of the shadow mask and the X-ray detector relative to one another can be determined by comparing the measurement signals of in each case two detector elements in two directions, in order to align the shadow mask and the X-ray detector relative to one another. The same is achieved when the hole with enlarged dimensions is, for example, square and extends over four detector elements, or when the hole is rectangular and extends over four or more than four detector elements. In this case, measurement signals of detector elements can be summed depending on direction, and sums of measurement signals can be compared in order to determine the adjusting direction and, if appropriate, the displacement path.

At least one embodiment of the invention provides that the holes with enlarged dimensions are preferably arranged in the edge region of the shadow mask. In this way, the holes with enlarged dimensions do not affect the imaging negatively, or have only an insignificant effect.

According to one variant of at least one embodiment of the invention, it is provided, depending on the X-ray detector, that whenever the X-ray detector has only detector elements with the same dimensions, apart from the holes of enlarged dimensions the shadow mask includes holes that also have substantially the same dimensions. If, by contrast, the X-ray detector has various groups of detector elements in which detector elements within the group have the same dimensions, but have different dimensions between the groups, the shadow mask is then also designed so as to adapt to the X-ray detector in such a way that it includes various groups of holes, the holes substantially having the same dimensions within the group, but having different dimensions between the groups.

According to one variant of at least one embodiment of the invention, depending on its intended use the shadow mask has round, oval, angular, rectangular, square and/or slot-shaped holes.

If the shadow mask is provided for an X-ray detector arranged on a curved surface, the shadow mask is likewise of curved design, the shadow mask being adapted to the curvature of the X-ray detector.

At least one embodiment of the invention provides that the shadow mask is produced from a metal or from a metal alloy.

The shadow mask may be provided for an X-ray computed tomography unit, it being optionally possible according to one variant of at least one embodiment of the invention for the shadow mask to be arranged upstream of an X-ray detector in the beam path of X-radiation emanating from an X-ray source. In the case of a third generation X-ray computed tomograph, for example, the shadow mask is arranged on the movable part of the gantry and can be brought into the beam path with the aid, advantageously, of stepping motors, or can be removed from the beam path of the X-radiation.

An object of at least one embodiment of the present invention relating to the method is achieved by way of a method for adjusting a shadow mask of the type described above over an X-ray detector, having detector elements, of an X-ray device. In this case, the shadow mask is first arranged over the X-ray detector in such a way that it is aligned coarsely over the X-ray detector. With the use of X-radiation, measurement signals of the detector elements are determined and assigned to the at least one hole of the shadow mask with enlarged dimensions. The shadow mask and the X-ray detector are finally adjusted relative to one another on the basis of a comparison of the measurement signals. According to one variant of at least one embodiment of the invention, the shadow mask and the X-ray detector are adjusted relative to one another until at least substantially a prescribed result is yielded from the comparison of the measurement signals.

Starting once again, from an X-ray detector with detector elements of the same dimensions, and considering, for the sake of simplification, firstly only one hole with enlarged dimensions which is assigned to two detector elements of the X-ray detector, the shadow mask and the X-ray detector are aligned precisely relative to one another whenever the measurement signals of two detector elements exhibit the ratio 1:1, or the difference is zero. According to one variant of at least one embodiment of the invention, a number of holes with enlarged dimensions are used in order to align the shadow mask and the X-ray detector precisely relative to one another, the measurement signals of the detector elements respectively assigned to such a hole being compared. Finally, the shadow mask and the X-ray detector can be aligned relative to one another with the aid of the comparisons, it being possible for the adjustment path adjusting the shadow mask and the X-ray detector relative to one another to be determined from the determined measurement signals of the detector elements as a function of the position of the detector elements relative to one another.

According to at least one embodiment of one embodiment of the invention, sums of measurement signals are formed for the comparison in the case of the use of a hole with enlarged dimensions that extends over four or more detector elements.

When use is made of holes that extend over a number of detector elements, it is provided according to one variant of at least one embodiment of the invention to average over the measurement signals of the respective detector elements as a function of the required combination of measurement signals in order to reduce the influence of measured data noise when determining the adjusting direction and/or the adjustment path using the measurement signals.

BRIEF DESCRIPTION OF THE DRAWINGS

An example embodiment of the invention is illustrated in the attached schematics, in which:

FIGS. 2 to 7 show plan views of various combinations of shadow masks and X-ray detectors.

DETAILED DESCRIPTION OF THE EXAMPLE EMBODIMENTS

Figure 1:
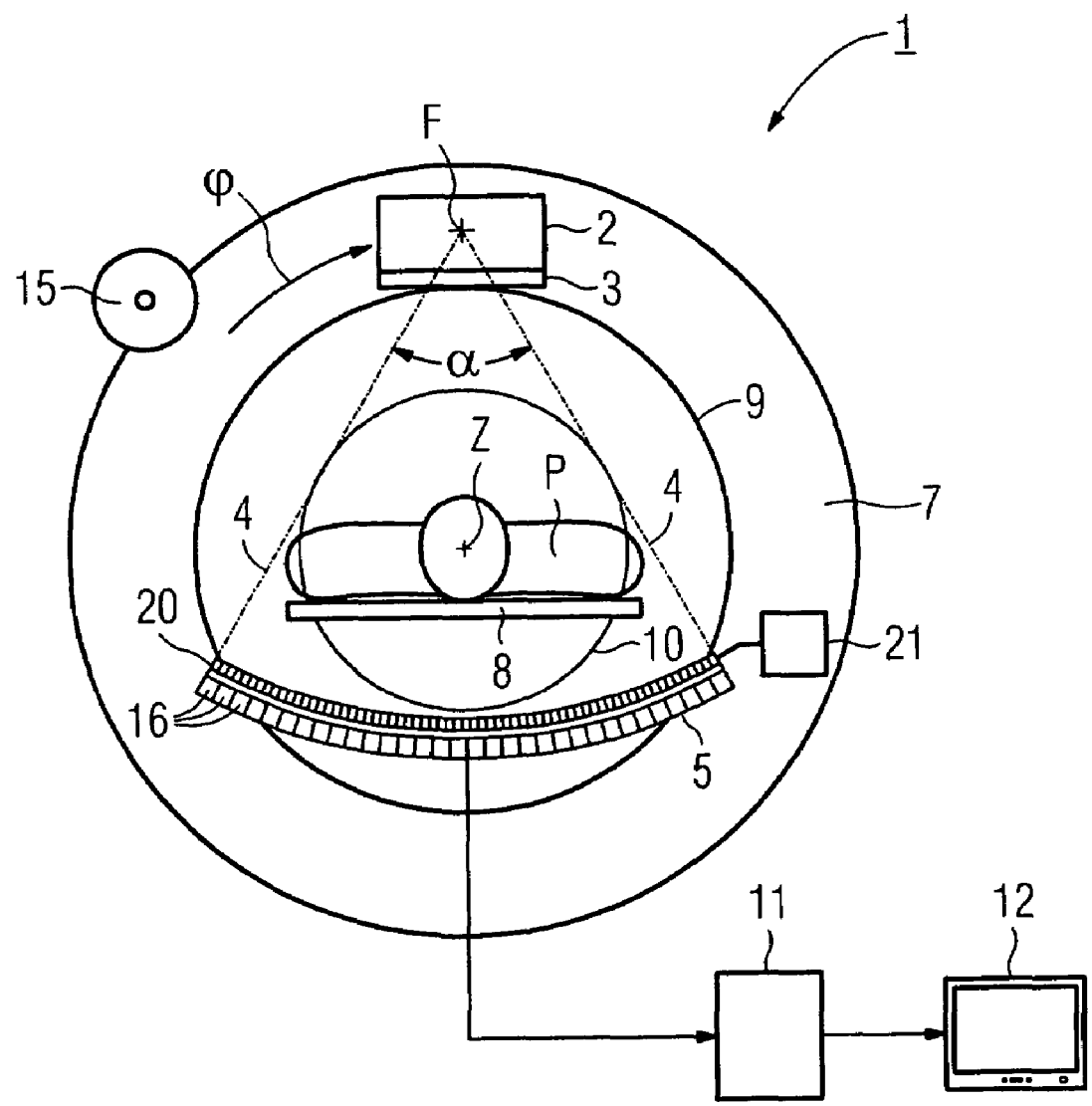
FIG. 1 shows a schematic, partial block diagram, of a computed tomography unit according to at least one embodiment of the invention.

The X-ray computed tomography unit 1 illustrated in FIG. 1 has an X-ray source in the form of an X-ray tube 2 from the focus F of which there emanates X-radiation that is shaped with the aid of a stop 3 to form a fan-shaped or a pyramidal-shaped X-ray beam 4 with an aperture angle $\alpha$. Arranged opposite the X-ray tube 2 is an X-ray detector 5 that, in the case of the present example embodiment, has a multiplicity of detector modules 16 that are arranged here substantially in the $\phi$-direction and in the z-direction next to one another. However, the detector module 16 can also be arranged one behind the other only substantially in the $\phi$-direction. Each detector module 16 includes in a way known per se a number of rows of detector elements 6 arranged following one another in the direction of the system axis z of the computed tomography unit.

The X-ray tube 2 and the X-ray detector 5 are arranged on a rotary frame 7, the rotating part of the gantry of the computed tomography unit 1. The rotary frame 7 is driven via an electric motor 15 in a way illustrated schematically in FIG. 1.

The computed tomography unit 1 further has a patient couch 8 on which a patient P to be examined is supported in the case of the present example embodiment. The patient couch 8 can be adjusted in the direction of the system axis z of the computed tomography unit 1 in a way known per se, this being moved through a patient opening 9 of the rotary frame 7 of the computed tomography unit 1.

The rotary frame 7 is mounted in a fashion capable of rotating about the system axis z of the computed tomography unit 1, and is rotated about the system axis z in the φ-direction in order to trans-irradiate the patient P with X-radiation, X-ray projections of a body region of the patient P being recorded from different projection directions. Here, the X-ray beam 4 includes a measuring field 10 of circular cross section.

While the patient P is being examined, X-radiation attenuated after passage through the patient P impinges on the detector element 6 of the detector module 16 of the X-ray detector 5. In the process, measurement signals from the detector elements 6 of the X-ray detector 5 are produced per X-ray projection as a consequence of the impinging X-radiation, and are fed to a computer 11. The computer 11 is used in a way known per se to reconstruct from the measurement signals of the detector element 6 tomographs or volumetric representations of recorded body regions of the patient P which can be displayed on a display apparatus 12.

In the case of the present example embodiment, the computed tomography unit 1 further includes a shadow mask 20 that is upstream of the X-ray detector 5, is arranged in the beam path of the X-radiation emanating from the X-ray tube 2, and has substantially the same curvature as the X-ray detector 5. The shadow mask 20 serves to increase the resolution of images of the patient P produced with the aid of the computed tomography unit 1.

Since the shadow mask 20 is not necessary for all methods of measurement and/or examination, it can be brought into the beam path of the X-radiation with the aid of one or more stepping motors 21, and removed from the beam path of the X-radiation again. In the case of the present example embodiment, like the shadow mask 20 itself, the stepping motors 21 are arranged on the rotary frame 7 of the computed tomography unit 1. The stepping motors 21 can move the shadow mask 20 inter alia in the direction of the z-axis and along the X-ray detector 5, and thus bring the shadow mask 20 into the beam path of the X-radiation and/or remove it from the beam path of the X-radiation.

Particularly in order to be able, with the aid of the shadow mask 20, to increase the resolution of an image produced with the aid of the computed tomography unit 1 in the case of digital recording methods, it is necessary to arrange the shadow mask as precisely as possible over the X-ray detector 5. Shown in FIGS. 2 to 7 by way of example in each case with the aid of a detector module 16 of the X-ray detector 5 are various combinations of shadow masks and X-ray detectors which are used to explain the precise alignment or adjustment of a shadow mask and the X-ray detector 5 relative to one another. The illustrations shown in FIGS. 2 to 7 are plan views in this case.

A detector module 16, having detector elements 6, of the X-ray detector 5 is illustrated with dashed lines in FIG. 2. The detector elements are, for example, directly converting detector elements or detector elements that have an X-ray scintillator and a photodiode.

As is to be seen from FIG. 2, a detector module 16 includes nine detector rows arranged one behind the other in the z-direction, each detector row having eleven detector elements 6. In the case of the present example embodiment, all the detector elements 6 have substantially the same dimensions, that is to say the same detector surface.

Shown at a preferably defined spacing above the detector module 16 is a section of the shadow mask 20 from FIG. 1 that is assigned to the detector module 16 shown, which shadow mask has a mask plate 18 that, in the case of the present example embodiment, is constructed from a metallic material, for example from tantalum, tungsten or from alloys of these materials. Apart from adjusting holes 22 to 25, the mask plate 18 of the shadow mask 20 includes square holes 19 that all have substantially the same dimensions and are arranged at equidistant steps from one another.

The holes 19 are adapted here to the dimensions of the detector elements 6 of the detector modules 16 of the X-ray detector 5. Thus, the holes 19 do not have the same dimensions as the detector elements 6, but have dimensions reduced in such a way that the X-radiation emanating from the X-ray tube 2 is applied respectively only to a part of the detector surface of the detector element 6 given precise alignment of the shadow mask 20 over the X-ray detector 5. The shadow mask 20 thus effects a reduction in the detector surface made available on the part of the X-ray detector 5.

As is to be gathered from FIG. 2, the section of the shadow mask 20 is not yet precisely aligned over the detector module 16 of the X-ray detector 5. Present in order to accomplish this in the corners of the section of the shadow mask 20 are the enlarged adjusting holes 22 to 25, which have already been mentioned and which have dimensions such that each of the four adjusting holes 22 to 25 extend over two detector elements 6 of the detector module 16 given precise alignment of the section of the shadow mask 20 over the detector module 16 of the X-ray detector 5.

The dimensions of the adjusting holes 22 to 25 are selected such that the X-radiation passing through the holes 22 to 25 substantially strikes the detector surface of the same size on the two relevant detector elements, given a precise alignment of the section of the shadow mask 20 over the detector module 16. For instance, looking by way of example at the detector elements 6.1, 6.2 in FIGS. 2 and 3, the alignment of the section of the shadow mask 20 over the detector module 16 is precise whenever, as is to be seen in FIG. 3, the hole 22 is aligned relative to the detector elements 6.1, 6.2 in such a way that X-radiation is applied in each case to the same surface fraction of the two detector elements 6.1, 6.2.

In terms of production engineering, the shadow mask 20 is aligned over the X-ray detector 5 in such a way that the shadow mask 20 is firstly aligned coarsely over the X-ray detector 5, for example oriented at the edges of the shadow mask 20 and the edges of the X-ray detector 5. In practice, the coarse positioning is performed under program control with the aid of the stepping motors 21. Such a case is illustrated in FIG. 2 with the aid of the detector module 16.

Subsequently, in the absence of the patient P X-radiation is emitted by the X-ray tube 2, preferably in a pulsed fashion, in the direction of the shadow mask 20 or the X-ray detector 5, and the measurement signals of the detector elements 6.1 and 6.2 as well as of the other detector element pairs (6.3, 6.4), (6.5, 6.6) and (6.7, 6.8) used to align the shadow mask 20 and the X-ray detector 5 relative to one another are determined with the aid of the computer 11. For example, the ratio of the measurement signals is formed for each detector element pair (6.1, 6.2) to (6.7, 6.8), and this ratio is compared with a prescribed ratio of the measurement signals.

Since, in the case of the present example embodiment, the detector elements 6 have substantially the same dimensions, and the dimensions of the adjusting holes 22 to 25 are selected such that X-radiation is applied substantially to the same detector surfaces of the detector elements 6.1 to 6.8 given precise alignment of the shadow mask 20 with the X-ray detector 5, the ratio 1:1 must be yielded for the detector element pairs (6.1, 6.2) to (6.7, 6.8) when the shadow mask 20 is aligned precisely over the X-ray detector 5. Here, when aligning or adjusting the shadow mask 20 the procedure is such that, depending on the fixed ratio of the measurement signals of the detector element pairs, the shadow mask 20 is adjusted with the aid of the stepping motors 21 until the ratio of the measurement signals of 1:1 has essentially been yielded for the detector element pairs (6.1, 6.2) to (6.7, 6.8). As shown in part in FIG. 3, the shadow mask 20 is aligned in this case precisely over the detector modules 16 of the X-ray detector 5.

The alignment of the shadow mask 20 relative to the X-ray detector 5 in the y-direction of the Cartesian coordinate system illustrated in FIG. 2 has been explained with the aid of FIGS. 2 and 3. Should it be necessary also to align the shadow mask 20 in the z-direction relative to the X-ray detector 5, a modified shadow mask has to be used, as illustrated by way of example in part in FIGS. 4 to 6. In order to be able to arrange the shadow mask precisely over an X-ray detector 5 in the z-direction as well, in addition to the adjusting holes 22 to 25, which extend over two detector elements and are aligned in the y-direction, the section of a shadow mask 30 shown in FIG. 4 has to have four further adjusting holes 26 to 29, which extend over two detector elements and are aligned in the z-direction.

The dimensions of the adjusting holes 26 to 29 are selected in a corresponding way to the dimensions of the adjusting holes 22 to 25. Consequently, the alignment of the shadow mask 30 in the z-direction can also be monitored via the X-ray detector 5, and the precise alignment can be brought about by using X-radiation and forming the ratio of the measurement signals for the detector element pairs (6.9, 6.10) to (6.15, 6.16).

Figure 4:
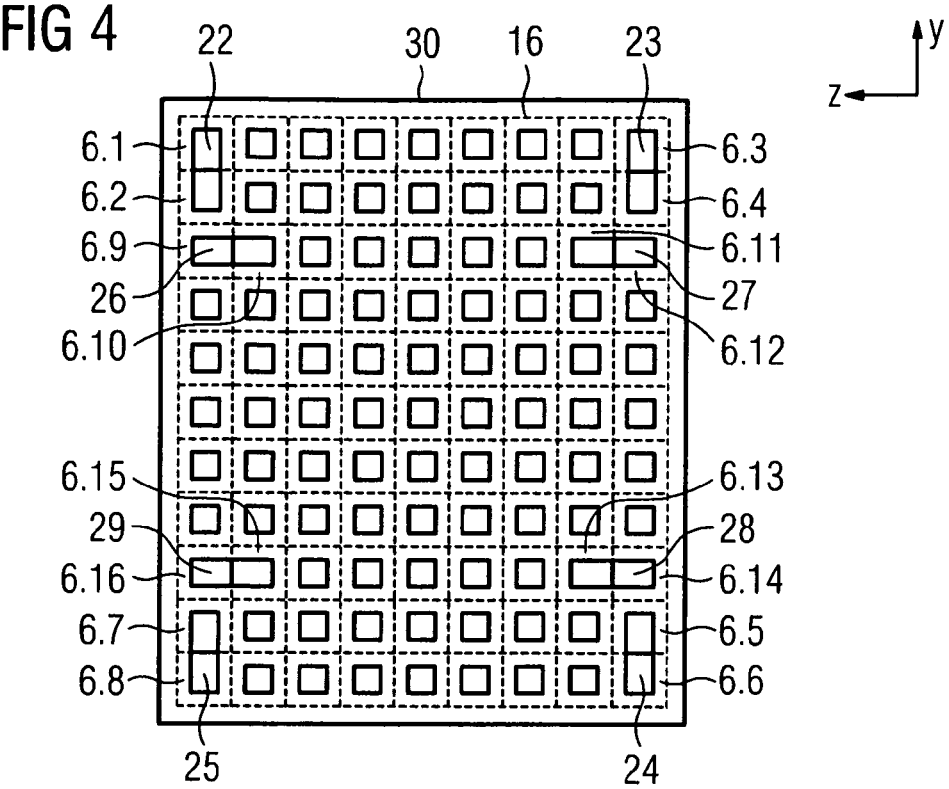

As illustrated in FIG. 4 for the present example embodiment, a ratio of 1:1 must then be yielded for the measurement signals at least substantially for all the detector element pairs (6.9, 6.10) to (6.15, 6.16). Even if, as previously described, the ratio of the measurement signals of the detector element pairs (6.1, 6.2) to (6.7, 6.8) is 1:1, the shadow mask 30 is aligned precisely over the X-ray detector 5.

Figure 5:
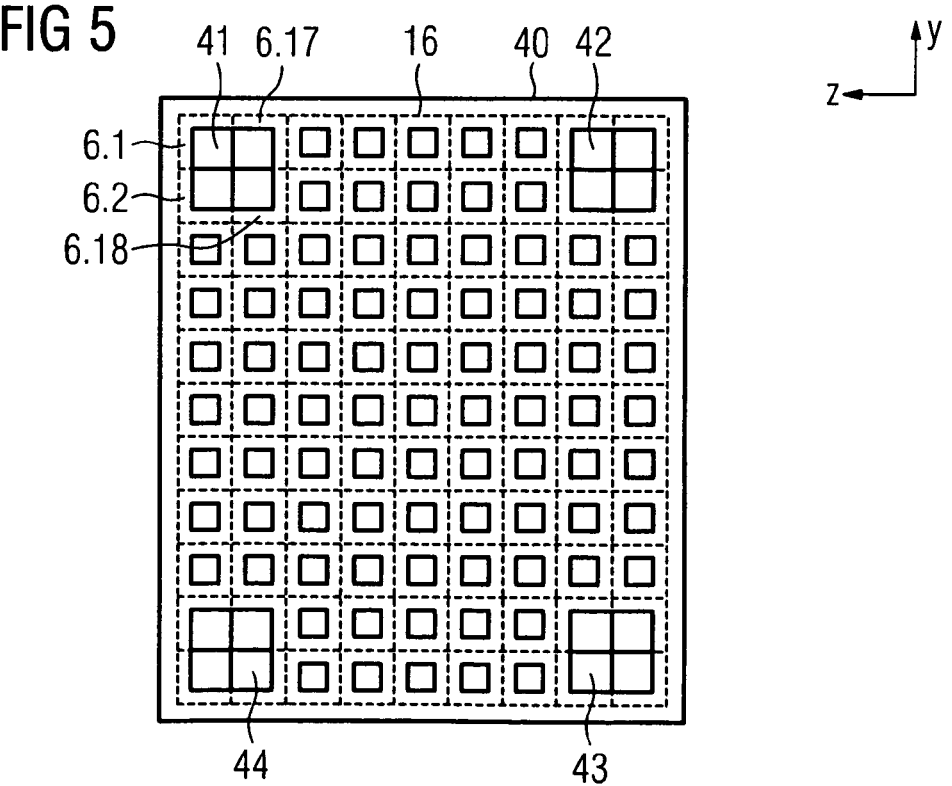

FIG. 5 shows a section of a further shadow mask 40 that, for the purpose of precise alignment over the detector module 16 or over the X-ray detector 5, respectively has an adjusting hole with enlarged dimensions at its four corners, each of the square adjusting holes 41 to 44 extending in this case over four detector elements of the detector module 16 of the X-ray detector 5. The measurement signals of the in each case four detector elements lying under the adjusting holes 41 to 44 are evaluated in order to align the shadow mask 40 in z- and y-directions. The signal evaluation is described by the example for the detector elements 6.1, 6.2, 6.17, 6.18 assigned to the hole 41.

In order to align in the y-direction, for example, the sum of the measurement signals of the detector elements 6.1 and 6.17, and the sum of the measurement signals of the detector elements 6.2 and 6.18 are formed, and the ratio of these sums is formed. If the result of such a procedure for all detector element groups assigned to the adjusting holes 41 to 44 is the ratio 1:1, the shadow mask 40 is aligned in the y-direction.

There is a comparable procedure with reference to alignment in the z-direction, explained by way of example in this case with reference to the detector elements assigned to the hole 41 by forming the sum of the measurement signals of the detector elements 6.1, 6.2 and the sum of the measurement signals of the detector elements 6.17, 6.18 and evaluating the ratio of the sums. If the ratio 1:1 is yielded in such a procedure for all the detector elements assigned to the adjusting holes 41 to 44, the shadow mask 40 is also aligned in the z-direction over the X-ray detector 5.

Illustrated in FIG. 6 is a section of a shadow mask 50 that has in its corner regions rectangular adjusting holes 51 to 54 that respectively extend over eight detector elements of the detector module 16 of the X-ray detector 5 in the case of the example embodiment illustrated in FIG. 6. The alignment of the shadow mask 50 relative to the X-ray detector 5 is performed here, as described above, such that sums of measurement signals are formed as a function of the direction of the alignment and are compared with corresponding sums.

In order to reduce the measured data noise when aligning the shadow mask 50 over the X-ray detector 5 on the basis of measurement signals, it is also possible here to average over a number of measurement signals. The mean values can be compared with one another subsequently.

By way of example for the adjusting holes 51 to 54, this may be explained for the adjusting hole 51 of the shadow mask 50 from FIG. 6, in which case in order to align the z-direction, for example, averaging is carried out over the measurement signals of the detector elements 6.1, 6.2, 6.9, 6.19 and over the measurement signals of the detector elements 6.17, 6.18, 6.20, 6.21. Subsequently, the relationship between the mean values is found, and the adjustment of the shadow mask 50 in the z-direction is accomplished as a function of the ratio obtained until the ratio of the mean values is 1:1.

The same approach can be used in the case of the adjusting holes 52 to 54. The alignment in the y-direction is also comparable. For example, it is possible here to carry out averaging for the adjusting hole 51 over the measurement signals of the detector elements 6.1, 6.2, 6.17, 6.18 and over the measurement signals of the detector elements 6.9, 6.19, 6.20, 6.21. The relationship between the mean values is then found in order to align the shadow mask 50. A corresponding procedure is adopted for the adjusting holes 52 to 54.

FIG. 7 additionally illustrates a combination of shadow mask and X-ray detector with the aid of a section of a shadow mask 80 and of a detector module 70, the detector modules 70 that form the X-ray detector having groups of detector elements with different dimensions. Thus, the detector elements of the detector element rows 71, 72 have the same dimensions per se. The situation is comparable for the detector element rows 73 and 74 or 75 and 76.

With reference to its holes, the shadow mask 80 is adapted in this case to the dimensions of the detector elements of the detector module 70. In a way comparable to the previously described shadow masks, so as to align it over the X-ray detector the shadow mask 80 has adjusting holes with enlarged dimensions in order to be able to align the shadow mask 80 precisely over the X-ray detector by way of measurement signals. Thus, the holes 81 to 84 serve to align in the y-direction, and the holes 85 and 86 serve to align the shadow mask 80 in the z-direction.

As already described for the other combinations of shadow masks and X-ray detector, in this case the measurement signals of the relevant detector elements are evaluated and their ratio is preferably found. The method described above for adjusting a shadow mask and an X-ray detector relative to one another can thus also be applied to X-ray detectors and/or shadow masks whose detector elements have dimensions differing from one another.

The measurement signals were compared above by forming the ratios of measurement signals, sum signals or averaged signals. However, it is also possible to compare the measurement signals in another way, for example in the form of a difference operation.

It goes without saying that a shadow mask for an X-ray detector can have adjusting holes of various types, as described above. Moreover, instead of angular holes it is also possible to provide round, oval and/or slot-shaped holes as adjusting holes.

In addition to determining the ratio of the measurement signals with the aid of which the adjustment of the shadow mask can be performed, the ratio determined can also be used to calculate the respective adjustment path directly. If the dimensions of an adjusting hole are known, the dimensions of the projection surfaces on the relevant detector elements are also known, neglecting the vertical distance between the shadow mask and the X-ray detector. Finally, the adjustment path can be calculated for the shadow mask, by way of example, from the ratio of the measurement signals and the knowledge that X-radiation is applied to the same detector surface fractions of the relevant detector elements given precise alignment of the shadow mask over the X-ray detector.

By way of example, a consideration with the aid of FIGS. 2 and 3 of the alignment of the shadow mask 20 in the y-direction over the X-ray detector 5 with the aid of the adjusting hole 22 yields an adjustment path of ⅙*10 mm, that is to say 1.67 mm, in the negative y-direction given a length of the adjusting hole 22 in the y-direction of 10 mm, and a ratio of the measurement signals of the detector elements 6.1 and 6.2 of 2:1 [(⅔ fraction of 10 mm): (⅓ fraction of 10 mm)]. For the other adjusting holes, this calculation can be carried out in a corresponding way not only for the shadow mask 20, but also for the shadow mask 30, 40, 50 and 80. The adjustment path can be calculated in each case in this way.

The alignment of the shadow mask and of the X-ray detector relative to one another will preferably first be performed in the first direction, for example y-direction, and subsequently in the second direction for example z-direction. The stepping motors are used in this case for the alignment.

The X-ray detector can also be adjusted relative to the shadow mask as an alternative to adjusting the shadow mask relative to the X-ray detector.

For the purpose of simplified illustration, FIGS. 2 to 7 respectively illustrate sections of shadow masks that form a coherent shadow mask together with other sections. It goes without saying that not every section of a shadow mask assigned to a detector module 16 need be provided with adjusting holes. Preferably, it is only in the edge regions that the sections of a shadow mask have one or more adjusting holes that are assigned to the detector modules or detector elements arranged at the edge of the X-ray detector.

Moreover, a shadow mask need not extend over the entire X-ray detector, either. Rather, a shadow mask can also be provided only for a specific region, for example the middle, of the X-ray detector.

Neither need the X-ray detector necessarily be constructed from detector modules.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for adjusting a shadow mask over an X-ray detector, including detector elements, of an X-ray device, the shadow mask including holes with dimensions substantially adapted to dimensions of at least one detector element to which the hole is assigned, at least one hole having dimensions enlarged to be adapted to the dimensions of at least two detector elements, the method comprising:

arranging the shadow mask over the X-ray detector such that the shadow mask is aligned coarsely over the X-ray detector;

determining, using X-radiation, measurement signals of the detector elements which are assigned to said at least one hole with a larger dimension of the shadow mask; and adjusting the shadow mask and the X-ray detector relative to one another, based upon a comparison of the measurement signals of the detector elements.

2. The method as claimed in claim 1, wherein the shadow mask and the X-ray detector are adjusted relative to one another until at least substantially a prescribed result is yielded from the comparison of the measurement signals.

3. The method as claimed in claim 2, wherein a number of holes with enlarged dimensions are used, and the measurement signals of the detector elements respectively assigned to a hole are compared.

4. The method as claimed in claim 2, wherein the adjustment path for adjusting the shadow mask and the X-ray detector relative to one another is determined from the comparison of the measurement signals of the detector elements as a function of the position of the detector elements relative to one another.

5. The method as claimed in claim 1, wherein a number of holes with enlarged dimensions are used, and the measurement signals of the detector elements respectively assigned to a hole are compared.

6. The method as claimed in claim 1, wherein the adjustment path for adjusting the shadow mask and the X-ray detector relative to one another is determined from the comparison of the measurement signals of the detector elements as a function of the position of the detector elements relative to one another.

7. The method as claimed in claim 1, wherein sums of measurement signals are formed for the comparison in the case of the use of a hole with enlarged dimensions that extends over four or more detector elements.

8. The method as claimed in claim 7, wherein a number of detector elements are averaged over the measurement signals.

* * * * *